(12) United States Patent
Chaudhuri et al.

(10) Patent No.: US 11,865,087 B2
(45) Date of Patent: *Jan. 9, 2024

(54) COMPOSITIONS AND METHODS FOR REDUCING HAIR LOSS AND INCREASING HAIR GROWTH

(71) Applicant: Sytheon Ltd, Boonton, NJ (US)

(72) Inventors: Ratan K Chaudhuri, Lincoln Park, NJ (US); Manpreet Randhawa, Robbinsville, NJ (US)

(73) Assignee: Sytheon Ltd, Parsippany, NJ (US)

( * ) Notice: Subject to any disclaimer, the term of this patent is extended or adjusted under 35 U.S.C. 154(b) by 153 days.

This patent is subject to a terminal disclaimer.

(21) Appl. No.: 17/392,223

(22) Filed: Aug. 2, 2021

(65) Prior Publication Data
US 2022/0008360 A1 Jan. 13, 2022

Related U.S. Application Data

(63) Continuation-in-part of application No. 16/059,425, filed on Aug. 9, 2018, now Pat. No. 11,077,035.

(60) Provisional application No. 62/544,433, filed on Aug. 11, 2017.

(51) Int. Cl.
*A61K 31/12* (2006.01)
*A61P 17/14* (2006.01)
*A61K 9/00* (2006.01)

(52) U.S. Cl.
CPC ............ *A61K 31/12* (2013.01); *A61K 9/0014* (2013.01); *A61P 17/14* (2018.01)

(58) Field of Classification Search
CPC .... A61K 31/12; A61K 9/0014; A61K 9/7015; A61P 17/14
See application file for complete search history.

(56) References Cited

U.S. PATENT DOCUMENTS 11,077,035 B2 * 8/2021 Chaudhuri ............... A61K 8/37

* cited by examiner

*Primary Examiner* — Robert A Wax
*Assistant Examiner* — Quanglong N Truong
(74) *Attorney, Agent, or Firm* — Hoffmann & Baron, LLP; Edward K Welch, II (57) ABSTRACT

Method of mitigating or reversing the effect of alopecia comprising applying select aryl alkanones to those areas of the skin suffering hair thinning and/or loss.

20 Claims, 3 Drawing Sheets

| Before using serum | 3 months after using hair serum |

Figure 3

FIG. 4A – IL-17A Down-Regulated Genes

FIG. 4B – IL-17A Up-Regulated Genes

COMPOSITIONS AND METHODS FOR REDUCING HAIR LOSS AND INCREASING HAIR GROWTH

RELATED APPLICATIONS

The present application is a Continuation-In-Part of U.S. patent application Ser. No. 16/059,425 filed Aug. 9, 2018, entitled "Hair Treatment Compositions and Methods," now U.S. Pat. No. 11,077,035, which claims the benefit of U.S. Provisional Patent Application No. 62/544,433 filed Aug. 11, 2017, entitled "Hair Treatment Compositions and Methods," the contents of both of which are hereby incorporated herein by reference in their entirety.

FIELD OF THE INVENTION

The present disclosed subject matter relates to compositions and methods for maintaining and/or improving scalp health, for maintaining and/or improving hair health, and for maintaining, promoting, and/or rejuvenating hair growth. In particular, the present disclosed subject matter relates to scalp and hair treatments comprising aryl alkanones and their use in order to promote and restore scalp health, to mitigate eyebrow and hair loss and increase hair and eyebrow health and growth.

BACKGROUND OF THE INVENTION

Scalps are usually hidden by hair and very easy to overlook unless one is dealing with alopecia (hair loss) or dandruff or hair graying. But at second glance, scalps are so much more—they're at the magical intersection where skin care happens to overlap with hair care, which means everyone's favorite obsession can be further expanded in the pursuit of better hair. One should treat the scalp the way one treats skin, and the latest lineup of scalp-specific products were designed with that crossover in mind. The idea is that the healthier the scalp, the healthier the hair. Hair loss or alopecia can result from a number of causes and factors including the failure to regrow hair fibers from existing hair follicles, extrafollicular environmental factors that affect follicular stem cell activity, and from the loss of hair follicles (HFs) themselves.

Mammalian hair, wherever located on the body, e.g., scalp, eyebrows, eyelids (upper and lower), face, legs, arms, etc., goes through a regular growth cycle consisting of four phases, anagen, catagen, telogen and exogen, the latter coinciding with and overlapping the anagen phase of the following growth cycle. The duration of each phase is dependent upon a number of factors including, the location of the hair on the body, sex, age, genetics, diet, health, etc. During the anagen phase, the hair follicle, specifically the dermal papilla, which contains blood vessels for supplying nutrients to the hair and cells which produce hair growth regulating hormones, and the germinal matrix, form the new hair. The duration of anagen phase determines the length and thickness of the hair and is dependent upon continued proliferation and differentiation of matrix cells at the follicle base. Again, depending upon a number of factors, most especially the location of the hair, the anagen phase may last for several months, as in the case of eyebrow hair, or many years, as is the case for scalp hair. Eventually, the supply of matrix cells declines, differentiation of hair shaft (HS) and inner root sheath (IRS) slows down, and the follicle enters a relatively short lived, days to a couple weeks, retrogressive or destructive phase called catagen in which hair formation and growth stops. Often this is evident from a thinning of the hair strand at the base and/or loss of color. Following catagen, the follicles lie dormant in a resting phase known as the telogen phase, which is of intermediate duration, typically on the many weeks or months: typically, up to four months for scalp hair. Thereafter, the follicle enters the exogen phase which is typified by the loss or expulsion of the hair strand. Of course, hair strand loss can occur anytime, and does, however, the majority of hair strands are lost during this phase. Concurrent with the exogen phase, the new anagen phase commences whereby, typically, the new hair strand is already starting to grow at the base of the follicle while the old hair strand is expelled from the top of the follicle and, thus, the cycle repeats. The body is constantly making new hair so most people do not notice the shedding and renewal.

Despite this renewal process, hair thinning and pattern hair loss, androgenetic alopecia (AGA), and spot or clump hair loss, alopecia areata (AA), are common happenstances affecting humans, particularly as one ages, and are most frequently caused by a failure to activate existing hair stem cells during hair cycling. Among the less common hair loss diseases or conditions are alopecia total is (AT) in which all hair on the scalp is lost and alopecia universal is (AU) in which all scalp and body hair is lost: these latter two are often considered advanced forms of alopecia areata, which is also commonly referred to localized alopecia areata. Whereas AA, AT and AU involve rapid and sudden hair loss, in typical androgenetic alopecia (AGA), hair fibers become progressively thinner and then fail to regenerate. AGA, which is the most common form of hair loss, is reversible, particularly at early stages, but may become irreversible after continued disease progression. In general, it is believed that hair thickening and growth can be rescued or at least mitigated if the general follicular structure is preserved and the causative factor is removed.

Although less common than AGA, though certainly more common than AT and AU, AA affects about 5.3 million people in the United States alone, including males and females across all ethnic groups. [Cooper G S et al, Recent insights in the epidemiology of autoimmune diseases: improved prevalence estimates and understanding of clustering of diseases. *J. Autoimmun*, 33:197-207, 2009]. Collectively, AA, AT and AU are prevalent chronic and relapsing autoimmune diseases, which target the hair follicles (HFs) and, as noted above, are characterized by the sudden appearance of patches of hair loss on the scalp or other locations on the body [Alkhalifah A, et al., *Alopecia areata update: part I. Clinical picture, histopathology, and pathogenesis. J Am Acad Dermatol* 62:177-188, 2010, quiz 189-190; Alkhalifah A, et al., *Alopecia areata update: part II. Treatment. J Am Acad Dermatol* 62:191-202, 2010, quiz 203-194; Pratt C H, et al, *Alopecia areata. Nat Rev Dis Primers* 3:17011, 2017]. While the loss of hair is drastic enough, such sudden and extensive the loss also has a devastating effect on one's quality of life and mental health. [Paus R & Arck P, *Neuroendocrine perspectives in alopecia areata: does stress play a role? J Invest Dermatol* 129:1324-1326, 2009; Picardi A et al, *Psychosomatic factors in first-onset alopecia areata. Psychosomatics* 44:374-381, 2003]

While much progress has been made in recent years in our understanding the pathobiology of AA and its related diseases, it is not fully understood: a fact that hampers the development of effective treatments [Biran R, et al, *The genetics of alopecia areata: new approaches, new findings, new treatments, J Dermatol Sci* 78:11-20, 2015; McElwee K J, et al, *What causes alopecia areata? Exp Dermatol* 22:609-626, 2013; Ramot Y & Zlotogorski A, *Molecular genetics of alopecia, Curr Probi Dermatol* 47:87-96, 2015; Renert-Yuval Y & Guttman-Yassky E, *The changing landscape of alopecia areata: the therapeutic paradigm. Adv Ther* 34:1594-1609, 2017]. Clearly, manifestation of AA has a strong genetic predisposition [Biran R et al, *The genetics of alopecia areata: new approaches, new findings, new treatments. J Dermatol Sci* 78:11-20, 2015]; however, environmental and psychological stimuli also play key roles in triggering the disease [McElwee K J et al, *What causes alopecia areata? Exp Dermatol* 22:609-626, 2013; Wasserman D et al, *Alopecia areata. Int J Dermatol* 46:121-131, 2007]. Other causes may be found as well as further research advances.

Although regrowth of the hair may occur as spontaneous as its loss in cases of AA, the likelihood is low, particularly with AT and AU. Accordingly, various treatments have been proposed and evaluated, but with limited, if any, success. For example, topical treatments such as corticosteroids, tacrolimus, cryotherapy, minoxidil, anthralin, or ultraviolet light A combined with oral psoralens (PUVA), have all failed to demonstrate robust evidence for their consistent efficacy in AA and are generally unsuitable for extensive cases of AA because of such minimal efficacy [J Shapiro, *Current treatment of alopecia areata. J Invest Dermatol Symp Proc*, 16(1):S42-S44, 2013; FM Delamere et al., Interventions for alopecia areata, Cochrane Database Syst Rev, 2008(2): CD004413; C Schmoeckel et al., *Treatment of alopecia areata by anthralin-induced dermatitis. Arch Dermatol*, 115(10):1254-1255, 1979; J Shapiro, *Dermatologic therapy: alopecia areata update, Dermatol Ther.* 2011; 24(3):301, 2011; J Shapiro, *Alopecia areata. Update on therapy, Dermatol Clin*, 11(1):35-46, 1993]. Contact sensitizers, such as diphenylcyclopropenone (DPCP), have also been considered as a topical immunotherapy and have been used abundantly with some efficacy; however, they appear to be associated with significant local adverse events, including vesicular reaction, pain, and scalp and facial edema [J Shapiro, *Dermatologic therapy: alopecia areata update, Dermatol Ther.* 2011; 24(3):301, 2011; J Shapiro, *Alopecia areata. Update on therapy, Dermatol Clin*, 11(1):35-46, 1993]. Intralesional injections of corticosteroids are often effective; but these can only be considered for patients with limited involvement [S P MacDonald et al., *British Association of Dermatologists Guidelines for the management of alopecia areata. Br J Dermatol*, 149(4):692-699, 2003].

Given the limited options and mixed results with approved treatments, owing to the devastating stigmatism and mental stress suffered by AA patients, they oftentimes are willing to risk significant adverse drug effects in an effort explore the efficacy of and to make off-label use of various therapeutic treatments intended for other diseases and conditions. Such off-label treatments include systemic corticosteroids (given as continuous or pulse therapy), cyclosporine A, mycophenolate mofetil, methotrexate as a monotherapy or in conjunction with corticosteroids, and azathioprine. All of these regimens are not FDA-approved for AA, and lack large, randomized placebo-controlled data for efficacy and safety in AA [SP MacDonald Hull et al., *British Association of Dermatologists Guidelines for the management of alopecia areata. Br J Dermatol*, 149(4):692-699, 2003; KY Park et al., *Combination therapy with cyclosporine and psoralen plus ultraviolet a in the patients with severe alopecia areata: a retrospective study with a self-controlled design, Ann Dermatol*, 25(1):12-16, 2013; EA Olsen et al., *Systemic steroids with or without 2% topical minoxidil in the treatment of alopecia areata, Arch Dermatol*, 128(11):1467-1473, 1992; S Farshi S et al., *Could azathioprine be considered as a therapeutic alternative in the treatment of alopecia areata? A pilot study, Int J Dermatol*, 49(10):1188-1193, 2013; R Shreberk-Hassidim et al., *A systematic review of pulse steroid therapy for alopecia areata. J Am Aced Dermatol*, 74(2):372-4 e1-5, 2016]. While these are all commonly used, these drugs have problematic safety profiles, with major systemic adverse effects and variable degree of immunosuppression, as well as rapid recurrence of hair loss following drug cessation, and are therefore unsuitable for the chronic nature of extensive AA [A Gilhar et al., *N Engl J Med*, 366(16):1515-1525, 2012]. In sum, despite being a relatively common condition, AA, including its extensive form, lacks good treatment options. Better clinical management with improved therapeutic modalities for AA, and particularly for widespread disease, is therefore highly desired.

Alopecia areata is a T-cell-mediated disease that shares phenotypic similarities with certain other inflammatory diseases, particularly atopic dermatitis (K Malik and E Guttman-Yassky, *Cytokine targeted therapeutics for alopecia aereta: Lessons from atopic dermatitis and other inflammatory skin diseases, J Invest Dermatology*, 19:S62-S64, 20218). One of the pro-inflammatory cytokines, interleukin-17 (IL-17), has gained much interest in recent years, due to its significant role in the pathogenesis of a large number of inflammatory and autoimmune disorders including rheumatoid arthritis, multiple sclerosis, inflammatory bowel disease, asthma, and psoriasis [J F Wright at al, *The Human IL-17F/IL-17A Heterodimeric Cytokine Signals through the IL-17RA/IL17RC Receptor Complex, J Immunol*, 181(4): 2799-2805, 2008]. Several more recent studies have found elevated serum levels of IL-17 and T-helper 17 (Th-17) including:

Han et al. who evaluated Th17 cells in the blood of 177 patients and compared them to 42 healthy controls [Han Y M et al, *Imbalance of T-helper 17 and regulatory T cells in patients with alopecia areata. J Dermatol* 42:981-988, 2015].

Atwa et. al. whose examination of 47 AA patients showed significantly elevated serum levels of IL-17 as compared to 40 matched healthy controls [Atwa M A et al, *T-helper 17 cytokines (interleukins 17, 21, 22, and 6, and tumor necrosis factor-alpha) in patients with alopecia areata: association with clinical type and severity. Int J Dermatol* 55:666-672, 2016].

El-Morsy et al. who found elevated IL-17 serum levels 39 AA patients as compared to 37 healthy controls [El-Morsy E H et al, *Serum level of interleukin-17A in patients with alopecia areata and its relationship to age. Int J Dermatol* 55:869-874, 2016].

Elela M A et al. who found elevated IL-17 serum levels 40 AA patients as compared to 40 healthy controls [Elela M A et al, *B cell activating factor and T-helper 17 cells: possible synergistic culprits in the pathogenesis of alopecia areata. Arch Dermatol Res* 308:115-121, 2016].

With the occurrence of such findings, consideration is now being given to potentially targeting IL-17 inhibition in addressing alopecia areata (AA) [Ramot Y et al, *IL-17 inhibition: is it the long-awaited savior for alopecia areate? Arch Dermatol Res*, 310:383-390, 2018]. In following, there are a few case reports which suggest that the use of select biologics having IL-17 inhibitory activity, for example, secukinumab, ustekinumab and tofacitinib, induce scalp hair growth and hair darkening [Yajima et al, *Case Reports*

*Dermatol,* 11:82-85, 2019; Craiglow B G & King B A, *J Invest Dermatol,* 134:2988-2990, 134]. Biologics, however, have many limitations and adverse consequences, such as, toxic side effects; method of delivery (injection vs topical); immunosuppressive; changed pharmacokinetics of biologics; drug resistance in less than 2 yrs.; serious infections; short shelf life; requires refrigeration, continuous laboratory monitoring; adherence issues & high cost.

Granted, there are existing, approved treatments for hair loss including finasteride and minoxidil and, while these are effective in arresting the progression of the disease, they allow only partial regrowth of hair at its best [K York, N Meah, B Bhoyrul, R Sinclair, A review of the treatment of male pattern hair loss, *Expert Opin Pharmacother,* 21(5): 603-612, 2020]. Hence, while some progress has been and is being made, there are still extensive and growing unmet needs for addressing and treating the manifestation of alopecia, whatever form, and various scalp diseases and maladies.

Accordingly, there is a continuing need for therapeutic agents and actives that will address the cause or underlying factors that lead to alopecia and various scalp diseases and maladies. Most especially, therapeutic agents and actives that will restore health, integrity and/or performance of the skin of the scalp and/or eyebrow region and their function, thereby reducing hair loss and thinning and increasing hair growth and health.

There is a continuing need for therapeutic agents and actives that will enhance the restoration of scalp and/or eyebrow region suffering from hair loss and/or thinning, whether due to aging, malady, trauma, environmental exposure and attack, etc., and their function, thereby reducing hair loss and thinning and increasing hair growth and health There is a continuing need for therapeutic agents and actives that have broad applications, especially addressing fundamental hair related scalp and eyebrow defects and maladies arising from auto-immune processes, most especially auto-immune diseases and conditions.

There is a continuing need for therapeutic agents and actives that will restore scalp function, particularly follicular function, for visibly smoother, fuller and more radiant-looking hair.

There is an urgent need for therapeutic agents and actives having the properties and performance as recited above, which are simple and cost effective and do not require multi-step synthesis or extraction and isolation techniques.

There remains a need for scalp, eyelid, and eyebrow treatment compositions that achieve any or all of the foregoing objectives formulations and that are easy to use with highly efficacious results.

There remains a need for scalp, eyelid, and eyebrow treatment compositions that achieve any or all of the foregoing objectives formulations without adverse side effects and/or or other health related concerns.

There remains a need for treatment compositions that overcome or mitigate the effects and manifestations of alopecia, most especially, androgenic alopecia, alopecia areata, alopecia totalis and/or alopecia universalis.

Finally, there remains a need for scalp treatment compositions based on synergistic combinations of agents or actives wherein the overall amount of the agents to be used are less than would be needed with either agent on their own.

SUMMARY

Surprisingly, it has now been found that the application, especially topical application, of certain aryl alkanones to areas of the skin, most notably the scalp and eyebrow region, promotes hair growth resulting in a fuller looking head of hair and eyebrows. Additionally, its application to areas of the skin suffering from alopecia is found to counteract hair loss and/or thinning resulting from the alopecia and/or promote new hair growth where hair growth had stopped. Not intending to be bound thereby, it is believed that this effect is, at least in part, a result of the inhibition of interleukin-17 and/or the up-regulation/stimulation and/or expression of various growth factors associated with hair growth including, but not limited to, Insulin Growth Factor 1 (IGF-1), Platelet-derived Growth Factor B (PDGFβ), Fibroblast Growth Factor 1 and 7 (FGF-1 and 7), Vascular Endothelial Growth Factor (VEGF).

Specifically, there is provided a method of promoting and/or stimulating hair growth, particularly on the scalp, eyelid and the eyebrow region, comprising applying to those areas of the skin, particularly the scalp, eyelids, or eyebrow region, where one desires to provide for fuller and/or healthier hair, particularly thicker hair, one or more aryl alkanones corresponding to the general Structure 1

Structure 1 wherein $R_1$, $R_2$, $R_3$, $R_4$ and $R_3$, which may be the same or different, are independently H, OH, alkyl or alkoxy wherein the alkyl or alkoxy groups are linear or branched and have from 1 to 8 carbon atoms, preferably from 1 to 6 carbon atoms, most preferably from 1 to 4 carbon atoms; and $R_6$ is H, $COCH_3$ or $CO_2R_7$, wherein $R_7$ is a linear or branched alkyl having 1 to 8 carbon atoms, preferably from 1 to 6 carbon atoms, most preferably from 1 to 4 carbon atoms. Most preferably, the aryl alkanone is applied topically in a carrier or as a component of a skin care and/or cosmetic composition. The composition is applied directly to the skin, particularly in those hair covered areas of the skin where thicker hair is desired or those areas of the skin which hair is missing and where hair is desired, or to the base of the hair strands, including eyebrows, themselves.

In accordance with a second aspect of the present teaching there is provided a method of mitigating or counteracting/reversing the effects of alopecia, said method comprising applying to those areas of the body, particularly the scalp, eyelids, and eyebrow region of the face, which are manifesting and/or suffering from alopecia an effective amount of one or more aryl alkanones corresponding to the general Structure Structure 1 wherein $R_1$, $R_2$, $R_3$, $R_4$ and $R_5$, which may be the same or different, are independently H, OH, alkyl or alkoxy wherein the alkyl or alkoxy groups are linear or branched and have from 1 to 8 carbon atoms, preferably from 1 to 6 carbon atoms, most preferably from 1 to 4 carbon atoms; and $R_6$ is H, $COCH_3$ or $CO_2R_7$, wherein $R_7$ is a linear or branched alkyl having 1 to 8 carbon atoms, preferably from 1 to 6 carbon atoms, most preferably from 1 to 4 carbon atoms, in a dermatologically acceptable carrier.

In accordance with a third aspect of the present teaching there is provided a method of inhibiting interlueken-17 (IL-17) and/or modulating IL-17 downstream genes, particularly growth factor genes, and/or directly up-regulating or stimulating those cytokines and/or growth factors responsible for hair growth including Insulin Growth Factor 1 (IGF-1), Platelet-derived Growth Factor (PDGF), Fibroblast Growth Factor (FGF), and/or Vascular Endothelial Growth Factor (VEGF), said method comprising applying to those areas of the body in which hair growth promotion and/or stimulation is desired, particularly the scalp, eyelids, and eyebrow region of the face, an effective amount of one or more aryl alkanones corresponding to the general Structure 1

Structure 1 wherein $R_1$, $R_2$, $R_3$, $R_4$ and Rr, which may be the same or different, are independently H, OH, alkyl or alkoxy wherein the alkyl or alkoxy groups are linear or branched and have from 1 to 8 carbon atoms, preferably from 1 to 6 carbon atoms, most preferably from 1 to 4 carbon atoms; and $R_6$ is H, $COCH_3$ or $CO_2R_7$, wherein $R_7$ is a linear or branched alkyl having 1 to 8 carbon atoms, preferably from 1 to 6 carbon atoms, most preferably from 1 to 4 carbon atoms, in a dermatologically acceptable carrier.

In accordance with a fourth aspect of the present teaching there is provided topical compositions comprising two or more aryl alkanones corresponding to the general Structure 1

Structure 1 wherein $R_1$, $R_2$, $R_3$, $R_4$ and $R_5$, which may be the same or different, are independently H, OH, alkyl or alkoxy wherein the alkyl or alkoxy groups are linear or branched and have from 1 to 8 carbon atoms, preferably from 1 to 6 carbon atoms, most preferably from 1 to 4 carbon atoms; and $R_6$ is H, $COCH_3$ or $CO_2R_7$, wherein $R_7$ is a linear or branched alkyl having 1 to 8 carbon atoms, preferably from 1 to 6 carbon atoms, most preferably from 1 to 4 carbon atoms, which compositions manifest improved promotion and/or stimulation of hair growth, especially new hair growth, as compared to a composition wherein only one of the select aryl alkanones is present.

Finally, in accordance with a fifth aspect of the present teaching there is provided topical compositions comprising one or more aryl alkanones corresponding to the general Structure 1

Structure 1 wherein $R_1$, $R_2$, $R_3$, $R_4$ and $R_5$, which may be the same or different, are independently H, OH, alkyl or alkoxy wherein the alkyl or alkoxy groups are linear or branched and have from 1 to 8 carbon atoms, preferably from 1 to 6 carbon atoms, most preferably from 1 to 4 carbon atoms; and $R_6$ is H, $COCH_3$ or $CO_2R_7$, wherein $R_7$ is a linear or branched alkyl having 1 to 8 carbon atoms, preferably from 1 to 6 carbon atoms, most preferably from 1 to 4 carbon atoms, in combination with a known active for promoting or stimulating hair growth and/or new hair generation, most especially where the combination manifests an improved promotion and/or stimulation of hair growth as compared to each active individually, particularly a synergistic effect.

The compositions according to the present teaching as well as the compositions employed in the methods of the present teaching typically comprise the aryl alkanone(s), with or without the additional hair growth promoter, in a dermatologically acceptable carrier. Alternatively, the aryl alkanone(s) may be incorporated into a cosmetic or hair care product including shampoos, conditioners, eyebrow fillers, moisturizing compositions, sunscreens, and the like. Generally speaking, the aryl alkanone being present in an effective amount, preferably from 0.01 to 20, preferably from 0.05 to 10, more preferably, from 0.1 to 5, most preferably 0.1 to 2.5, weight percent, based on the total weight of the composition. Where a second, typically conventional, hair growth promoter is employed in the claimed compositions, it too is present in an amount of from 0.01 to 20, preferably from 0.05 to 10, more preferably, from 0.1 to 5, most preferably 0.1 to 2.5, weight percent, based on the total weight of the composition.

DETAIL DESCRIPTION OF THE INVENTION

As used in the present specification, the following terms shall have the meanings as presented:

A "dermatologically acceptable carrier" refers to a material that acts as a diluent, dispersant or carrier for the stated actives, especially the aryl alkanone(s), and is recognized in the industry as acceptable or suitable for use, preferably long term use, in skin contact and, to the extent appropriate or applicable, has been approved or is otherwise approvable by a regulatory agency of a government or governmental body or is listed in the U.S. Pharmacopoeia or other generally recognized pharmacopoeia for use on humans.

The term "improves" or "improved" is used to convey that the method and compositions of the present teaching manifest an improvement in hair growth and health, as well as scalp health, as compared to the untreated hair and skin. In particular, it is manifest in thicker hair and/or broader hair coverage as compared to the hair and treated areas prior to the application of the claimed compositions.

The term "modulating" generally refers to the ability of the claimed compositions to down-regulate, suppress or inhibit or, alternatively, up-regulate or stimulate the expression of the mentioned genes, cytokines, growth factors and the like, as appropriate.

The term "optional" or "optionally" means that the subsequently described subject, event or circumstance may or may not occur, and that the description includes instances where the event occurs and instances where it does not and/or when the subject is present and when it is not present.

The terms "effective amount" and "hair promoting effective amount" refer to the amount of the specified compound or composition that when applied to the skin is able to affect the desired effect whether on a molecular level, as evidenced by changes in the level or concentration of targeted materials, especially cytokines and other factors, and/or on a macro level whereby visual changes are evident with respect to hair growth and thickening.

Erring on the side of caution and in an effort to avoid having overlooked or inadvertently omitted certain descriptive matter, particularly complementary and supplementary descriptive matter, it is hereby stated and affirmed that the technical publications as well as the patent and patent application publications mentioned herein are all incorporated herein in their entirety by this reference. Indeed, for example, while the current specification could present page after page of description of suitable dermatologically acceptable vehicles, supplemental or ancillary ingredients, and co-actives as well as various cosmetic and skin care compositions into which the aryl alkanones can be incorporated, such would not be productive as the same are well known and well recognized by those skilled in the art and those that come into being subsequent to the filing of this application will readily be appreciated as suitable as well

According to a first embodiment, there is provided a method of promoting and/or stimulating hair growth, particularly on the scalp, eyelids, and the eyebrow region, comprising applying to those areas of the skin, particularly the scalp, eyelids, or eyebrow region, where one desires to provide for fuller and/or healthier hair, particularly thicker hair, one or more aryl alkanones corresponding to the general Structure 1

Structure 1 wherein $R_1$, $R_2$, $R_3$, $R_4$ and $R_5$, which may be the same or different, are independently H, OH, alkyl or alkoxy wherein the alkyl or alkoxy groups are linear or branched and have from 1 to 8 carbon atoms, preferably from 1 to 6 carbon atoms, most preferably from 1 to 4 carbon atoms; and $R_6$ is H, $COCH_3$ or $CO_2R_7$, wherein $R_7$ is a linear or branched alkyl having 1 to 8 carbon atoms, preferably from 1 to 6 carbon atoms, most preferably from 1 to 4 carbon atoms. Most preferably, the aryl alkanone is applied topically in a carrier or as a component of a skin care and/or cosmetic composition. The composition is applied directly to the skin, particularly in those hair covered areas of the skin where thicker hair is desired or those areas of the skin where hair is missing but desired, or to the base of the hair strands, including eyebrows and eyelashes, themselves.

In accordance with a second aspect of the present teaching there is provided a method of mitigating or counteracting the effects of alopecia, said method comprising applying to those areas of the body, particularly the scalp, eyelids, and eyebrow region of the face, which are manifesting and/or suffering from alopecia an effective amount of one or more aryl alkanones corresponding to the general Structure 1

Structure 1 wherein $R_1$, $R_2$, $R_3$, $R_4$ and $R_5$, which may be the same or different, are independently H, OH, alkyl or alkoxy wherein the alkyl or alkoxy groups are linear or branched and have from 1 to 8 carbon atoms, preferably from 1 to 6 carbon atoms, most preferably from 1 to 4 carbon atoms; and $R_6$ is H, $COCH_3$ or $CO_2R_7$, wherein $R_7$ is a linear or branched alkyl having 1 to 8 carbon atoms, preferably from 1 to 6 carbon atoms, most preferably from 1 to 4 carbon atoms, in a dermatologically acceptable carrier.

In accordance with a third aspect of the present teaching there is provided a method of inhibiting interlueken-17 (IL-17) and/or modulating those cytokines and/or growth factors responsible for hair growth including Insulin Growth Factor 1 (IGF-1), Platelet-derived Growth Factor (PDGF), Fibroblast Growth Factor (FGF), and/or Vascular Endothelial Growth Factor (VEGF), said method comprising applying to those areas of the body in which hair growth promotion and/or stimulation is desired, particularly the scalp, eyelids, and eyebrow region of the face, an effective amount of one or more aryl alkanones corresponding to the general Structure 1

Structure 1 wherein $R_1$, $R_2$, $R_3$, $R_4$ and $R_r$, which may be the same or different, are independently H, OH, alkyl or alkoxy wherein the alkyl or alkoxy groups are linear or branched and have from 1 to 8 carbon atoms, preferably from 1 to 6 carbon atoms, most preferably from 1 to 4 carbon atoms; and $R_6$ is H, $COCH_3$ or $CO_2R_7$, wherein $R_7$ is a linear or branched alkyl having 1 to 8 carbon atoms, preferably from 1 to 6 carbon atoms, most preferably from 1 to 4 carbon atoms, in a dermatologically acceptable carrier.

In accordance with a fourth aspect of the present teaching there is provided topical compositions comprising two or more aryl alkanones corresponding to the general Structure 1

Structure 1 wherein $R_1$, $R_2$, $R_3$, $R_4$ and $R_5$, which may be the same or different, are independently H, OH, alkyl or alkoxy wherein the alkyl or alkoxy groups are linear or branched and have from 1 to 8 carbon atoms, preferably from 1 to 6 carbon atoms, most preferably from 1 to 4 carbon atoms; and $R_6$ is H, $COCH_3$ or $CO_2R_7$, wherein $R_7$ is a linear or branched alkyl having 1 to 8 carbon atoms, preferably from 1 to 6 carbon atoms, most preferably from 1 to 4 carbon atoms, which compositions manifest improved promotion and/or stimulation of hair growth, especially new hair growth, as compared to a composition wherein only one of the select aryl alkanones is present.

Finally, in accordance with a fifth aspect of the present teaching there is provided topical compositions comprising one or more aryl alkanones corresponding to the general Structure 1

Structure 1 wherein $R_1$, $R_2$, $R_3$, $R_4$ and $R_5$, which may be the same or different, are independently H, OH, alkyl or alkoxy wherein the alkyl or alkoxy groups are linear or branched and have from 1 to 8 carbon atoms, preferably from 1 to 6 carbon atoms, most preferably from 1 to 4 carbon atoms; and $R_6$ is H, $COCH_3$ or $CO_2R_7$, wherein $R_7$ is a linear or branched alkyl having 1 to 8 carbon atoms, preferably from 1 to 6 carbon atoms, most preferably from 1 to 4 carbon atoms, in combination with a known active for promoting or stimulating hair growth and/or new hair generation, most especially where the combination manifests an improved promotion and/or stimulation of hair growth as compared to each active individually, particularly a synergistic effect.

Preferred compounds according to Structure 1 generally fall into four groups as follows:

Group A wherein $R_1$, $R_2$, and $R_5$ are H and $R_4$ is an alkyl or alkoxy group of from 1 to 8, preferably from 1 to 6, more preferably from 1 to 4 carbon atoms, most preferably $OCH_3$, and $R_6$ is H, $COCH_3$ or $CO_2C_2H_5$;

Group B wherein $R_1$ and $R_5$ are H, $R_2$ and $R_4$ are $OCH_3$, $R_3$ is OH, and Re is H, $COCH_3$ or $CO_2C_2H_5$;

Group C wherein $R_1$, $R_2$, and $R_5$ are H, $R_4$ is $OCH_3$, $R_3$ is OH, and $R_6$ is H, $COCH_3$ or $CO_2C_2H_5$; and Group D wherein $R_1$, $R_2$, and $R_5$ are H, $R$ and $R_3$ are alkoxy groups, which may be the same or different, of 1 to 8, preferably, 1 to 6, more preferably 1 to 4, carbon atoms, and Re is H, $COCH_3$ or $CO_2C_2H_5$.

The most preferred aryl alkanone compounds for use in the practice of the present teaching are those compounds of Structure 2:

Structure 2 wherein $R_2$, $R_3$, $R_4$ and $R_6$ are as described above.

Exemplary preferred aryl alkanone compounds include:
Compound 1 (Acetyl Zingerone): R is H; $R_3$ is OH; $R_4$ is $OCH_3$; and $R_6$ is $COCH_3$;
Compound 2: $R_2$ is H; $R_3$ is OH; $R_4$ is $OCH_3$; and $R_6$ is $CO_2C_2H_5$;
Compound 3: $R_2$ and $R_4$ are H; $R_3$ is OH; and Re is $COCH_3$;
Compound 4: $R_2$ and R are H; $R_3$ is OH; and Re is $CO_2C_2H_5$;
Compound 5: $R_2$ and $R_4$ are $OCH_3$; $R_3$ is OH; and Re is $COCH_3$;
Compound 6: $R_2$ and $R_4$ are $OCH_3$; $R_3$ is OH; and Re is $CO_2C_2H$;
Compound 7: $R_2$, $R_3$ and $R_4$ are $OCH_3$; and Re is $COCH_3$;
Compound 8: $R_2$. $R_3$ and $R_4$ are $OCH_3$; and Re is $CO_2C_2H_5$;
Compound 9: $R_2$ and $R_4$ are H; $R_3$ is $OCH_3$; and Re is $CO_2C_2H_5$;
Compound 10: $R_2$ and $R_4$ are H; $R_3$ is $OCH_3$; and Re is $COCH_3$;
Compound 11 (Methyl Acetyl Zingerone): $R_2$ is H; Re and $R_4$ are $OCH_3$; and Re is $COCH_3$;
Compound 12 (Raspberry Ketone): $R_2$ and $R_4$ are H; $R_3$ is OH; and $R_6$ is H; and
Compound 13 (Methyl Raspberry Ketone): $R_2$ and $R_4$ are H; $R_3$ is $OCH_3$; and Re is H.

Although the aryl alkanone(s) could be applied to the skin or hair directly, it is/they are typically applied as a component of a composition. Most preferably, the compositions according to the present teaching comprise the aryl alkanone in a dermatologically acceptable carrier or excipient and/or as a component of a skin or hair care product, as a component of a cosmetic composition, or as a component of a topically applied pharmaceutical composition.

Generally speaking, the aryl alkanones may be combined with/incorporated into any known carrier or base composition employed in skin or hair care/treatment compositions; especially those carriers and excipients that are suitable for long term and repeated application to the skin without manifesting sensitization or irritation or inflammation. Suitable carriers and excipients include any of the known topical excipients and like agents necessary for achieving the particular form of the skin care composition desired. Exemplary excipients include, e.g., mineral oils, silicone oils, and emulsifying agents as well as water, alcohol, or water/alcohol combinations, or other solvent(s) or solvent systems in which the aforementioned actives may be, e.g., soluble, dispersed, emulsified, etc. Preferably, though, the compositions according to the present teaching will include excipients and the like that create a substantially stable, homogenous composition and/or provide body, improved partition coefficient, and viscosity to the composition so that the aryl alkanone does not merely run off the skin once applied. Suitable carriers and carrier compositions are described at length in, for example, Gonzalez et. al.—U.S. Pat. No. 7,186,404; Aust et. al.—U.S. Pat. No. 7,175,834; Roseaver et. al.—U.S. Pat. No. 7,172,754; Simoulidis et. al.—U.S. Pat. No. 7,175,835; Mongiat et. al.—U.S. Pat. No. 7,101,536; Maniscalco—U.S. Pat. No. 7,078,022; Forestier et. al. U.S. Pat. Nos. 5,175,340, 5,567,418, 5,538,716, and 5,951,968; Deflandre et. al.—U.S. Pat. No. 5,670,140; Chaudhuri—U.S. Pat. Nos. 6,831,191, 6,602,515, 7,166,273, 6,936,735, and 6,699,463; Chaudhuri et. al.—U.S. Pat. Nos. 6,165,450 and 7,150,876; Bonda et. al. U.S. Pat. No. 6,962,692; Rodan et. al.—U.S. Pat. No. 9,144,434, Wang et. al. U.S. Pat. No. 5,830,441 and Auspitz et. al.—US 2007/0110685 A1.

The final form of these compositions and their method of manufacture depend, in part, upon the mode of administration as well as the other ingredients to be incorporated into the composition. Accordingly, the compositions containing the aryl alkanones may be in form of solutions, suspensions, emulsions, powders, creams, lotions, serums, gels, sustained-release formulations, aerosols, sprays, and the like. In following, the compositions may be prepared by means of conventional mixing, dissolving, granulating, dragee-making, levigating, emulsifying, suspending, etc. All of such options and methods are conventional in the art.

The compositions according to the present teaching as well as the compositions employed in the methods of the present teaching typically comprise the aryl alkanone(s), with or without the additional hair growth promoter, in a dermatologically acceptable carrier with the aryl alkanone being present in an effective amount. Alternatively, the aryl alkanone(s) may be incorporated into a cosmetic or hair care product including shampoos, conditioners, eyebrow fillers, moisturizing compositions, sunscreens, and the like. The aryl alkanone(s) are present in a hair promoting/hair growth stimulating effective amount, generally from 0.01 to 20, preferably from 0.05 to 10, more preferably, from 0.1 to 5, most preferably 0.1 to 2.5, weight percent, based on the total weight of the composition. Where a second, typically conventional, hair growth promoter is employed in the claimed compositions, it too is present in an amount of from 0.01 to 20, preferably from 0.05 to 10, more preferably, from 0.1 to 5, most preferably 0.1 to 2.5, weight percent, based on the total weight of the composition. Most preferably, when both the aryl alkanone(s) and a second, non-aryl alkanone hair growth promoter or stimulator are employed the amount of each is in the range of from about 0.1 to about 5 wt %, more preferably from about 0.1 to about 2.5 wt %, based on the total weight of the composition. In following, when both are present the weight ratio of the aryl alkanone(s) to the second, non-aryl alkanone hair growth or stimulating agent will vary depending upon the selection of the second, non-alkanone hair growth or stimulating agent loss, however, they will generally be present in a weight ratio of 20:1 to 1:20, preferably from 10:1 to 1:10, more preferably 5:1 to 1:5, most preferably 2:1 to 1:2.

Ideally, the combination of the aryl alkanone(s) and/or the combination of the aryl alkanone and the second, non-aryl alkanone hair growth promoter or stimulator, provides a synergistic result whereby, though the aforementioned ranges still apply, the effect of the combination in terms of improved hair thickness and/or growth is greater or more effective than for either active alone at the same level of application. In this respect, one is able to use less of the hair promotion or hair growth actives to achieve the same or better results than using the same amount of each alone. This also has the benefit of reducing the concerns or risks of sensitization, irritation, etc., while maintaining or achieving a high degree of hair loss reduction or regrowth effect.

As noted, the aryl alkanones are preferably incorporated into or combined with a carrier or other composition. Besides those mentioned above, suitable carriers also include formulated base compositions used in the preparation of, for example, scalp care health and beauty aid products, cosmetic compositions, pharmaceutical or therapeutic skin care products and the like. Such compositions have, as their primary objective, the application of the aryl alkanone(s) and, optionally, the second, non-aryl alkanone hair growth or stimulating active, for the purpose of promoting and/or stimulating hair growth. However, these compositions may be supplemented with other co-active ingredients, such as antioxidants, sunscreen actives, vitamins, anti-inflammatory agents, moisturizers, emollients, humectants, skin lighteners, anti-acne ingredients, compatible solutes and the like, and mixtures thereof, in their conventional amounts. Alternatively, or in addition thereto, these compositions may also include other ingredients that have no or little bearing upon the intended end-use or application of the treatment aspect of these compositions, but aid in the preparation and/or longevity thereof, such as solubilizers, surfactants, stabilizers, thickeners, preservatives, buffers, etc. and/or the aesthetic qualities thereof, e.g., dyes, perfumes, scents, opacifiers, colorants, etc.

Alternatively, as previously mentioned, the aryl alkanone can be incorporated into or added to existing skin and hair care products, including cosmetics, shampoos, hair conditioners, eye brow fillers, and the like where the aryl alkanone is a secondary active and/or hair growth and stimulation is a secondary consideration. This is particularly desirable as a preventative or mitigator to hair thinning and loss due to, among other causes, aging, dietary issues, pharmaceutical or their therapeutic treatments known to cause or be associated with hair thinning and/or loss, and the like.

It is impractical to attempt to list all of the ingredients which may be combined with the aryl alkanones and/or all the compositions into which the aryl alkanones may be incorporated. However, those skilled in the art will readily appreciate the same in light of the teaching hereof and the intended purpose for which the aryl alkanone is being applied.

The amount of the aryl alkanone, especially the aryl alkanone composition, to be applied is generally that amount which is sufficient to provide a thin film of the composition to the treated skin and/or to the hair, especially the roots of the hair, i.e., that portion of the hair at the skin line. Typically, a small quantity of the composition, for example from 0.1 to 5 ml, is applied to the skin/hair from a suitable container or applicator and spread over and/or rubbed into the skin using the hands or fingers or a suitable device. Preferably, the aryl alkanone composition is applied at least once, preferably at least twice, daily until the desired hair thickening/hair growth effect is attained and/or for so long as alopecia continues to manifest itself. Alternatively, the aryl alkanone composition is applied continually, as a daily ritual, to improve hair health, thickening and/or rejuvenation. In this regard, a user may adopt a routine of application of the aryl alkanone composition where the aryl alkanone is the key or a key active ingredient to address pre-existing hair thinning and/or hair loss until the desired effect is attained and then employ a hair care or cosmetic composition containing the aryl alkanone as a daily routine to maintain hair fullness and coverage and/or prevent hair loss or thinning. Although the focus of the discussion has been with the application of the compositions to the scalp, eyelid and eyebrow region, it is to be appreciated that the composition and method is applicable to any area of the body suffering from alopecia or where hair growth is desired including those specifically mentioned above as well as the pubic region, chest, underarms, etc.

Not intending to be bound thereby, it is believed that the hair growth and/or hair stimulating effect is, at least in part, a result of the down-regulation/inhibition of interleukin-17 or interaction between IL-17A and IL-17R (receptor of IL-17A) or the modulating of IL-17 downstream genes, especially those down-stream genes, that are down-regulated/inhibited or up-regulated/stimulated, respectively, by IL-17, especially IL-17A. Additionally, following on the foregoing and/or independent thereof, it is also believed that the aryl alkanones of the present teaching up-regulate/stimulate the expression of various growth factors, particularly growth factors associated with hair growth, including, but not limited to, Insulin Growth Factor 1 (IGF-1), Platelet-derived Growth Factor β (PDGFβ), Platelet-derived Growth Factor α (PDGFα), Fibroblast Growth Factor 1 and 7 (FGF-1 and 7), Vascular Endothelial Growth Factor (VEGF) by the specified aryl alkanones. Accordingly, it is believed that actives that influence these factors as well as concentrates, such as platelet concentrates, that contain these factors will act synergistically with the aryl alkanones of the present teaching. Other influencing factors and agents to be used in combination with the aryl alkanones, besides those already mentioned herein, include, but are not limited to, isosorbide esters, especially the diesters and linoleic acid esters and similar compounds as disclosed in, e.g., U.S. Pat. Nos. 8,496,917; 9,636,321 and 10,597,402, the contents of which are incorporated herein by reference, as well as various plant extracts including terminalia chebula extract, Phyllanthus embilica extract, and the like.

Preferred co-actives are ones providing a linoleic component to the composition, especially, one or more of linoleic acid, alinoleic ester, a linoleic glycoside and/or a linoleic glyceride, especially a triglyceride. Especially preferred is linoleic acid and/or a short chain, $C_1$ to $C_8$, esters, most especially ethyl linoleate. Alternatively, especially owing to their availability, ease of formation and use, and cost, one may use one or more long chain fatty acid, ester, glycoside and/or glyceride compositions having a high linoleic content, particularly those wherein the linoleic content is at least 30%, preferably at least 40%, more preferably at least 45%, by weight, or even higher levels such as at least 50%, preferably at least 60%, more preferably at least 65%, by weight. Generally speaking, the long chain fatty acids are characterized as having from 14 to 22 carbon atoms and may be saturated or unsaturated. As noted, their esters, especially short chain esters, as noted above, glycosides, and glycerides, especially triglycerides, are also suitable and efficacious as are combinations thereof with each other and/or with the long chain fatty acids. Furthermore, one may enhance the linoleic content of long chain fatty acid, ester, glycoside and/or glyceride compositions by adding one or more of linoleic acid, a linoleic ester, a linoleic glycoside and a linoleic glyceride.

Additionally, while one may, and may preferably, elect to use the individual linoleic compounds noted above, or combinations thereof, it is more typical to employ fatty acid oils obtained or derived from natural sources containing high levels of the linoleic compounds. Suitable oils include those disclosed in Orsavova, J. et. al., "Fatty Acids Composition of Vegetable Oils and Its Contribution to Dietary Energy Intake and Dependence of Cardiovascular Mortality on Dietary Intake of Fatty Acids," Int. J. Mol. Sci. 2015, 16, 12871-12890, which is incorporated herein by reference, especially the oils isolated from safflower, grape seed, *Silybum marianum*, hemp, sunflower, wheat germ, pumpkin seed, sesame, rice bran, almond, rapeseed, peanut, olive, and coconut. Table 1 presents the breakdown of the oleic acid, linoleic acid and linolenic acid content (% by weight) of some of the more preferred oils.

TABLE 1

Source of natural oils and typical fatty acid compositions*

| Oils | Oleic Acid | Linoleic Acid | Linolenic Acid |
|---|---|---|---|
| Safflower | 8-21 | 68-83 | <0.5 |
| Grapeseed | 12-25 | 60-75 | ~0.2 |
| Rosehip | 14-16 | 43-46 | 31-34 |
| Sunflower typical | 14-40 | 48-74 | ~0.4 |
| Sunflower special | ~85 | ~6 | <0.5 |
| Hemp | ~10 | ~52 | ~10 |
| Walnut | 25-35 | 45-60 | <1 |
| Sesame | 35-50 | 35-50 | <1% |
| Evening Primrose | 5-11 | 70-77 | <1% |
| Soybean | 17-30 | 48-58 | 5-11 |
| Wheat-germ | 12-23 | 52-59 | 3-10 |

*Reference: https://essentialoils.co.za/rosehip-analysis.htm

As noted, these natural oils are comprised of a plurality of different fatty acids, oftentimes a combination of unsaturated, mono-saturated and/or polyunsaturated long chain fatty acids. The oils may be used as is or further purified to isolate specific long chain fatty acids or mixtures thereof. Suitable fatty acid esters may be obtained by esterifying with wide range of alcohols, such methanol, ethanol, propanol, butanol, pentanol, hexanols, etc. and are also available commercially. Similarly, suitable fatty acid glycerides may be obtained by esterifying the long chain fatty acids with glycerol. Of course, it is to be appreciated that the long chain fatty acid, ester and glyceride compositions may contain other fatty acids and esters, particularly where they are already present in the starting materials.

EXAMPLES

Having described the invention in general terms, the following sets of examples will now demonstrate various embodiments of the inventive compositions and their use. In the following examples, unless otherwise indicated, all temperatures are set forth in degrees Celsius and all parts and percentages are by weight based on the total composition as applied to the scalp or eyebrow.

Example 1

A scalp serum (Composition 1) according to the present teaching was prepared having the composition as presented in Table 2.

TABLE 2

Composition 1

| INCI name | Trade Name/Supplier | % w/w |
|---|---|---|
| Phase A | | |
| Water | | 62.15 |
| Panthenol | Ritapan DL, 50%/Rita | 1.00 |
| Niacinamide | Niacinamide/DSM | 1.00 |
| Denatured Alcohol | Denatured/Alcohol/Quality Chemical | 15.00 |
| Polyquaternium-10 | Ritaquta 3000/Rita | 0.75 |
| Butylene Glycol | Jeechem Bugl/Jeen | 4.00 |
| Glycerin | Glycerin/Jeen | 3.00 |
| Dehydroacetic Acid & Benzyl Alcohol | Geogard 221/Lonza | 1.00 |
| Trisodium Ethylenediamine Disuccinate | Natrlquest E30/Innospec | 0.10 |
| Phase B | | |
| Ethoxydiglycol | Transcutol CG/Gattefosse | 8.00 |
| Acetyl Zingerone (Compound 1) | Synoxyl ® AZ/Sytheon/Present invention | 2.00 |
| Rasberry Ketone (Compound 12) | Synoxyl ® RK/Sytheon/Present invention | 2.00 |
| Total | | 100.00 |

Composition 1 was prepared by weighing each of the components of Phase A and combining them in a main kettle equipped with a homogenizer and heating, while mixing, to 50-55° C. Similarly, each of the components of Phase B were weighed and combined in a side kettle and heat with mixing to 45° C. Mix was continued in each kettle until all solids were dissolved. When both phases attained the proper temperature and were uniform, Phase B was added to Phase A and the combination mixed for 10-15 minutes. The resulting composition was found to have a pH 5.0 to 5.5.

Example 2

A second scalp serum (Composition 2) according to the present teaching was prepared having the composition as presented in Table 3, Composition 2A having Acetyl Zingerone (Compound 1) and Composition 2B having Methyl Acetyl Zingerone (Compound 11). These compositions were prepared according to the same procedure as Composition 1.

TABLE 3

Compositions 2A and 2B

| INCI name | Trade Name/Supplier | % w/w |
|---|---|---|
| Phase A | | |
| Water | | 64.15 |
| Panthenol | Ritapan DL, 50%/Rita | 1.00 |
| Niacinamide | Niacinamide/DSM | 1.00 |
| Polyquaternium-10 | Ritaquta 3000/Rita | 0.75 |
| Butylene Glycol | Jeechem Bugl/Jeen | 4.00 |
| Glycerin | Glycerin/Jeen | 3.00 |
| Water & Sodium Benzoate & Potassium Sorbate | Euxyl K 712/Schulke | 1.00 |
| Phase B | | |
| Ethoxydiglycol | Transcutol CG/Gattefosse | 23.00 |
| Acetyl Zingerone (Compound 1) or Methyl Acetyl Zingerone (Compound 11) | Synoxyl ® AZ/Sytheon/Present invention or Synoxyl ® inventionMAZ/Sytheon/Present | 2.00 or 2.00 |
| Total | | 100.00 |

Example 3

Figure 1:
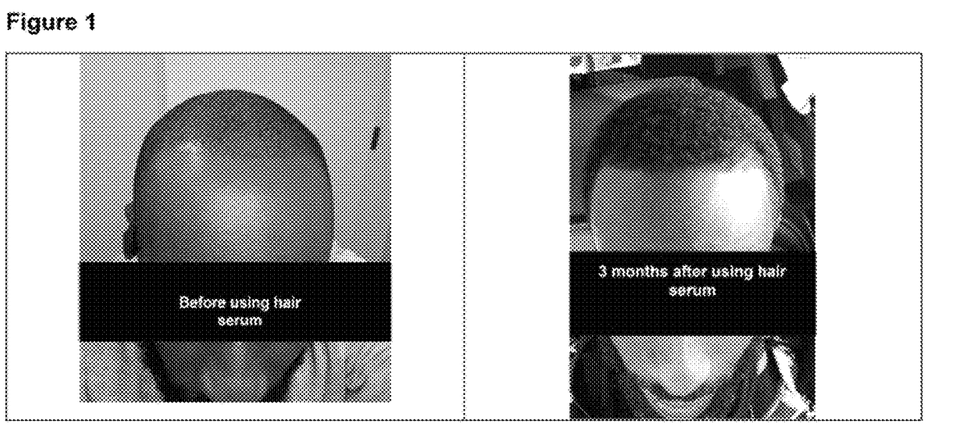
FIG. 1 presents before and after photographs of the scalp of a male individual to which a composition according the present teaching was applied.

An evaluation of the compositions according to the present teaching were applied to three male subjects to evaluate their effect in promoting hair growth and rejuvenation as follows:

Composition 1 was applied to the scalp of an African American individual (44 yrs. old male) twice a day for three months. He had been experiencing hair loss and had been bald for the last five years. He shows receding hairline on the front of the head and loss of hair on the crown of the head. He doesn't have any underlying skin conditions like eczema. Prior to the application of the Composition 1, the individual had applied Rogaine for a period of four months, but failed to see any growth. When using both Rogain and Composition simultaneously, significant hair growth and thickening was manifest as shown in FIG. 1.

Figure 2:
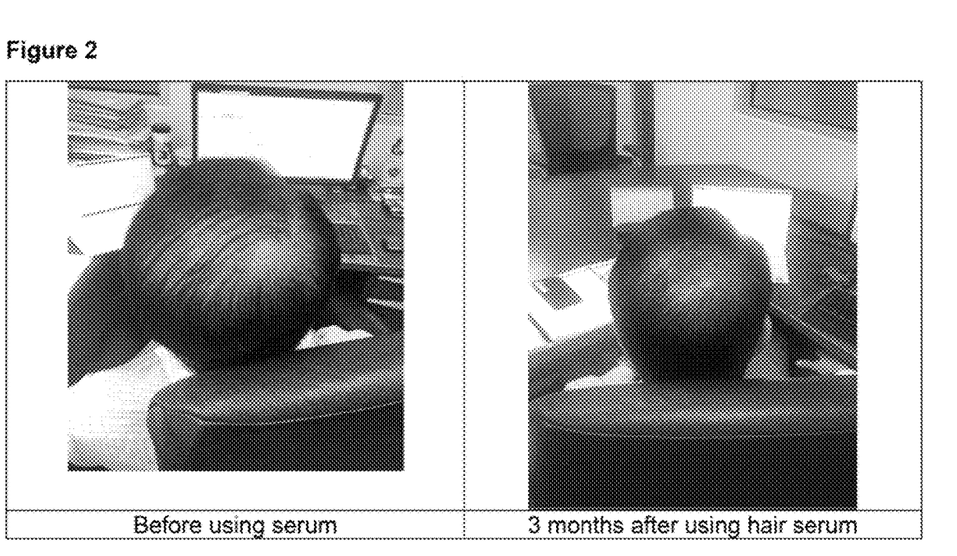
FIG. 2 presents before and after photographs of the scalp of a second male individual to which a composition according the present teaching was applied.

Composition 2A was applied to the scalp of an Asian American individual (75 year old male) twice a day for three months. As shown in FIG. 2, a significant improvement in hair growth and thickness was observed.

Figure 3:
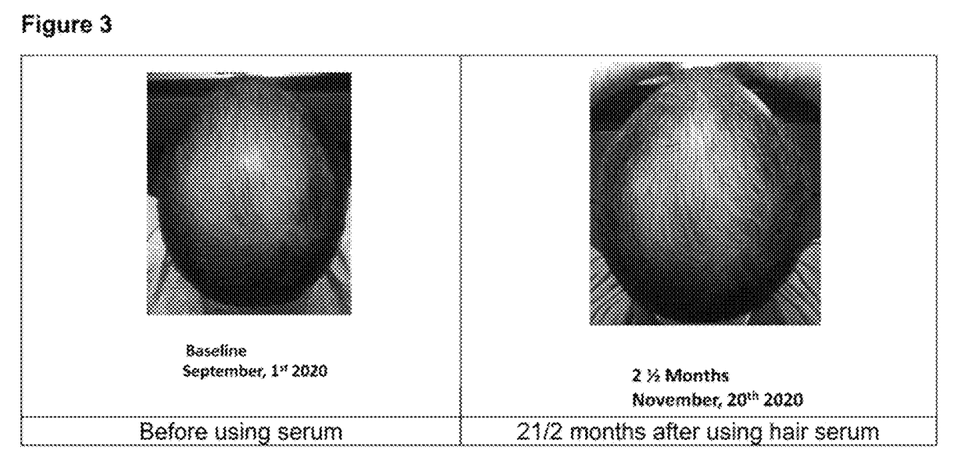
FIG. 3 presents before and after photographs of the scalp of a third male individual to which a composition according the present teaching was applied.

Composition 1 was applied to the scalp of a French individual (34 year old male) twice a day for two and a half months. As shown in FIG. 3, a significant improvement in hair growth and thickness was observed.

Example 4—Gene Assay—IL-17A Impact

Figure 4A:
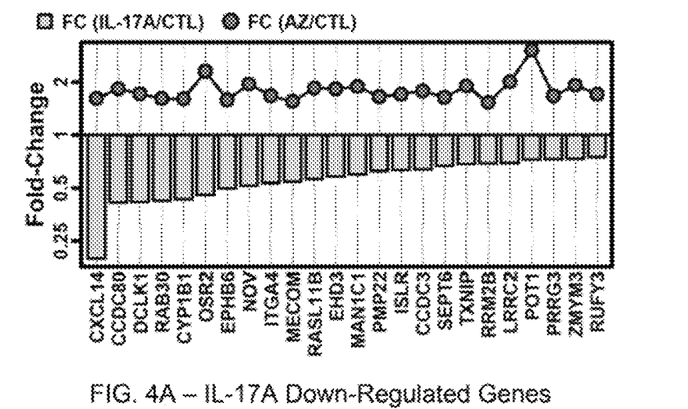
FIGS. 4A and 4B present in graph form a comparison of the impact of acetyl zingerone (AZ) and IL-17 on the up-regulation and down-regulation of various genes associated with hair growth.
Figure 4B:
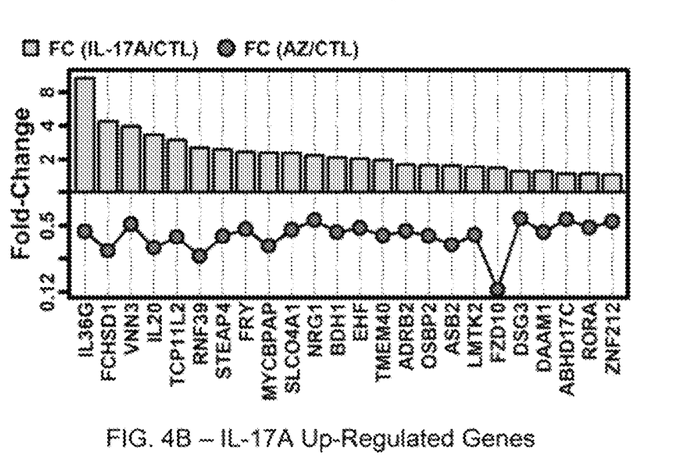

As noted in the Background, interleukin 17 (IL-17), particularly interleukin-17A (IL-17A), is believed to have a role in alopecia and its manifestation. In an effort to understand the possible effect of the aryl alkanones in impacting the effect of IL-17A, a microarray study was performed using RNA from EpiDerm FT (RHE) tissues (Mattek. Ashland, Mass.). In the experiment, standard methods of tissue processing and RNA extraction were followed. RNA obtained from cultures following 24 hours of exposure to acetyl zingerone (AZ-Compound 1) were analyzed using Agilent human 8X60K arrays (AZ, n=2; CTL, n=2). Microarray processing, normalization, quality control, probe annotation, probe filtering, differential expression testing, and motif/annotation enrichment analysis steps are followed as described in the literature (WR Swindell et al. *Psoriasis drug development and GWAS interpretation through in silico analysis of transcription factor binding sites, Clinical and translational medicine,* 4:13, 2015). As shown in FIGS. 4A and 4B, IL-17A had marked inhibitory and enhanced expression effect on a myriad of genes, particularly growth factor genes. Surprisingly, AZ had the opposite effect, providing a marked inhibitory effect on those genes whose expression was enhanced or up-regulated by IL-17A and a marked enhance or up-regulated effect on those genes inhibited or down-regulated by IL-17. These results are summarized in the FIGS. 4A and 4B. These results clearly demonstrated that IL-17A expression responses are markedly reduced by AZ and support the theorized mode of action of the AZ in terms of the inhibition of IL-17 and/or its down-stream regulation and impact upon hair related growth factors.

Example 5—Growth Factor Effect

A series of experiments were conducted to evaluate the effect on various aryl alkanones on several genes/growth factors specific to hair growth. Human hair follicle dermal papilla cell (HFDPC, lot #2905, cat.#602K-05a, obtained from a 46 year old Caucasian female) were purchased from Cell Applications, San Diego, Calif.) and were grown in the supplier-recommended medium until subconfluence. Cells were then seeded at 75,000/well in the 24 well plates and the next day they were exposed to different dilutions of test materials and their combinations. The treated culture were maintained for 24 h, after which they were observed through a Nikon inverted microscope. The cells were harvested and rinsed and RNA was extracted and purified with RNeasy Plus Mini kit cat. #74134 from Qiagen, (Germantown, Md.), using QiaCube Connect robotic station (Qiagen). Purified total RNA was assessed at 260 nm and 280 nm with NanoDrop Lite (Thermo Fisher Scientific, Waltham, Mass.). cDNA was prepared using High-Capacity RNA-to-cDNA™ Kit from Applied BioSystems (Carlsbad, Calif.) and the expression of the genes of interest, specifically IGF-1 and PDGFβ,) was measured by real-time quantitative PCR with BioRad iCycler iQ Detection System using TaqMan primer assays with FAM-labeled probes from Applied BioSystems and Azura 2×Taq Mix Master (Azura Genomics, Raynham, Mass.). Efficiency ΔΔCt method was used for quantification of results, after the normalization of gene expression to 18S (the housekeeping gene). Genes were considered differentially expressed if they were detected in at least one triplicate average (<50 cycles to detection), the p value, as determined by the two-tailed t-test, was ≤0.05 and the modulation was 22.0. To establish the optimal methods, multiple experiments were performed.

Table 4 presents the results of this study. The results are presented as the fold change (FC) of the expression of the indicated gene as compared to the water control: water being normalized. The results are considered statistically significant when p=<0.05. As shown in Table 4, the aryl alkanones, with the exception of raspberry ketone (RK) at low level, provided a marked upregulation of each of the growth factors, whereas the comparative compound, zingerone, manifested no effect. Accordingly, it is believed that an up-regulation of the various growth factors associated with hair growth may account for the hair growth and thickening realized by the use of the aryl alkanones of the present teaching. Although the results obtained with the combination of RK and AZ and RK and MAZ suggested a dilution or reduction in the effect of AZ and MAZ alone, the actual marked improvement in hair growth and thickening realized by the combination in Example 3 suggests that other growth factors may be more optimally up-regulated by RK and its combination with AZ and MAZ.

TABLE 4

| Test Material | P value | IGF-1 | p value | PDGFB |
|---|---|---|---|---|
| Water Control | 1 | 100 | 1 | 100 |
| Zingerone 50 ug/ml | | No effect | | No effect |
| Zingerone 200 ug/mL | | No effect | | No effect |
| AZ + RK 50 + 50 ug/mL | | No effect | 0.034 | 2.2 |
| MAZ + RK 100 + 100 ug/mL | | No effect | 0.000 | 4.0 |
| Raspberry Ketone (RK) 50 ug/mL | | No effect | | No effect |
| Raspberry Ketone (RK) 100 ug/mL | | No effect | 0.054 | 1.7 |
| Acetyl Zingerone (AZ) 50 ug/mL | 0.000 | 5.3 | 0.000 | 7.0 |
| Acetyl Zingerone (AZ) 100 ug/mL | 0.000 | 5.5 | 0.000 | 3.0 |
| Acetyl Zingerone (AZ) 200 ug/mL | 0.004 | 7.5 | | Not done |
| Methyl Acetyl Zingerone (MAZ) 50 ug/mL | 0.002 | 4.9 | 0.009 | 46 |
| Methyl Acetyl Zingerone (MAZ) 100 ug/mL | 0.000 | 8.0 | 0.001 | 5.7 |
| Methyl Acetyl Zingerone (MAZ) 200 ug/mL | 0.000 | 3.7 | 0.002 | 3.2 |

Example 6—Hair and Scalp Conditioner

In Examples 1 and 2, serum formulations were prepared for direct application to stimulate and promote hair growth, particularly for those suffering from alopecia areata. While those compositions are also efficacious and suitable for use on those individuals suffering from androgenetic alopecia, modified traditional hair care formulations are an alternative way to deliver the active for promoting growth, particularly for those in the early stages of androgenetic alopecia, particularly where large bald areas have yet to manifest. In following there is provided a hair and scalp condition formulated according to the formulation provided in Table 5. This formulation is prepared according to conventional general methodologies which typically comprises individually preparing Phases A and B and then combining the two and allowing the combined formulation to hydrate. Separately Phase C is prepared and heated to 80° C. After fully hydrating the combination of Phases A and B, the combination is heated to 75° C. and Phase C is gradually added while mixing. The mixture is then cooled under propeller agitation until cooled to 40° C. Meanwhile, Phase D is separately prepared and, once the combination of Phase A, B and C is cooled, Phase D is added to the mixture while maintaining mixing until uniform.

TABLE 5

Hair and Scalp Conditioner

| INCI name | % w/w |
|---|---|
| Phase A | |
| Water (demineralized) | 82.00 |
| Phase B | |
| Hydroxyethylcellulose | 1.00 |
| Glycerin | 2.00 |
| Cetrimonium Chloride | 0.50 |

TABLE 5-continued

Hair and Scalp Conditioner

| INCI name | % w/w |
|---|---|
| Phenoxyethanol | 1.00 |
| Potassium Sorbate | 0.25 |
| Phase C | |
| Glycery Stearate | 1.00 |
| Cetary Alcohol | 5.00 |
| Cetyl Esters | 0.50 |
| Behentrimonium Chloride | 1.00 |
| Isosorbide Dicaprylate | 2.00 |
| Caprylic/Capric Triglyceride | 0.50 |
| PEG-8 | 1.00 |
| Aryl Alkanone of Structure 1 | 0.50 |
| Phase D | |
| Panthenyl Hydroxypropyl Steardimonium Chloride | 0.30 |
| Panthenol | 0.30 |
| Hydrolyzed Rice Protein | 1.00 |
| Sodium Hydroxide | 0.15 |

Any of the aryl alkanones according to Structure 1, preferably of Structure 2, can be employed in the hair and scalp conditioner. Most preferably the aryl alkenone is acetyl zingerone, methyl acetyl zingerone, raspberry ketone, methyl raspberry ketone and combinations of any two, three or all four.

Example 7: Sunscreen Spray

One of the issues with alopecia of the scalp is that the scalp becomes more susceptible to sunburn. Accordingly, it is strongly recommended to apply a sunscreen to the scalp to protect it from sun damage. According to this example there is prepared a sunscreen spray formulation which not only protects against sunburn but also promotes hair growth and thickening. The exemplary formulation is presented in Table 6 and is prepared by preparing Phase A and a pre-mix of Phase B, the latter being heated to 75° C. with mixing until it is completely free of solids. Phases A and C are then added to phase B at 50° C. with continued mixing.

TABLE 6

Broad spectrum clear spray sunscreen

| INCI name | Trade Name/Supplier | % w/w |
|---|---|---|
| Phase A | | |
| Ethanol | Ethanol | 39.00 |
| VA/Butyl Maleate/Isobornyl Acrylate Copolymer | Advantage Plus/Ashland | 2.00 |
| Phase B | | |
| Avobenzone | Eusolex 9020/EMD | 3.00 |
| Trimethoxybenzylidene Pentanedione* | Synoxyl ® HSS/Sytheon | 2.50 |
| Homosalate | Eusolex HMS/EMD | 10.00 |
| Octyl Salicylate | Eusolex OS/EMD | 5.00 |
| Aryl Akanone | | 1.00 |
| PEG-8 | PEG 400/Acme | 5.00 |
| Diisopropyl Adipate | Dermol DIA/Alzo | 5.00 |
| Phase C | | |
| Phenethyl Benzoate | X-tend 226/Ashland | 20.50 |
| C12-15 Alkyl Benzoate | Finsolv TN/Innospec | 5.00 |
| Isosorbide Dicaprylate | HydraSynol ™ DOI/Sytheon | 2.00 |
| Total | | 100.00 |

*Trimethoxy benzylidene Pentanedione is as photostabilizer and in-vivo SPF booster. This can be replaced with Octocrylene or Diethylhexyl syringylidene malonate or Ethylhexyl mothocycrylene As with the hair and scalp conditioner of Example 6, any of the aryl alkanones according to Structure 1, especially Structure 2, can be employed in the instant sunscreen composition. Most preferably the aryl alkenone is acetyl zingerone, methyl acetyl zingerone, raspberry ketone, methyl raspberry ketone and combinations of any two, three or all four.

Example 8: Broad Spectrum Sunscreen Spray

A second, broad spectrum sunscreen spray formulation for use in the practice of the present teaching is of the formulation presented in Table 7. This product is produced in the same manner as the sunscreen composition of Example 7. Once again, as in Example 7, any of the aryl alkanones according to Structure 1, especially Structure 2, may be employed in the instant broad spectrum sunscreen spray. Most preferably the aryl alkenone is acetyl zingerone, methyl acetyl zingerone, raspberry ketone, methyl raspberry ketone and combinations of any two, three or all four.

TABLE 7

Broad spectrum clear spray sunscreen

| INCI name | Trade Name/Supplier | % w/w |
|---|---|---|
| Phase A | | |
| Ethanol | Ethanol | 39.00 |
| VA/Butyl Maleate/Isobornyl Acrylate Copolymer | Advantage Plus/Ashland | 2.00 |
| Phase B | | |
| Avobenzone | Eusolex 9020/EMD | 3.00 |
| Trimethoxybenzylidene Pentanedione | Synoxyl ® HSS/Sytheon | 2.50 |
| Homosalate | Eusolex HMS/EMD | 10.00 |
| Octyl Salicylate | Eusolex OS/EMD | 5.00 |
| PEG-8 | PEG 400/Acme | 8.00 |
| Diisopropyl Adipate | Dermal DIA/Alzo | 2.00 |
| Phase C | | |
| Phenethyl Benzoate | X-tend 226/Ashland | 20.50 |
| C12-15 Alkyl Benzoate | Finsolv TN/Innospec | 5.00 |
| Isosorbide Disunflowerseedate | HydaSynol ™ IDL/Sytheon | 2.00 |
| Total | | 100.00 |

The patents, patent publications and other documents cited herein, including any cross-referenced or related patent or patent applications, are hereby incorporated herein by reference in their entirety unless expressly excluded or otherwise limited. The citation of any document is not an admission that it is pertinent prior art with respect to any invention disclosed or claimed herein or that it alone, or in combination with any other citation or combination of citations, teaches, suggests or discloses any such invention.

Further, to the extent that any meaning or definition expressly applied to a term in this document conflicts with any meaning or definition of the same term in a document incorporated by reference, the meaning or definition assigned to that term in this document shall govern.

The various embodiments described above are provided by way of illustration only and should not be construed as or deemed to limit the claims attached hereto. The present invention can suitably comprise, consist of, or consist essentially of, any of the disclosed or recited elements. Thus, the invention illustratively disclosed herein can be suitably practiced in the absence of any element, which is not specifically disclosed as being required herein. Furthermore, various modifications and changes to the teachings herein will be recognized by those skilled in the art having the benefit of the present teachings and may be made to the present teachings without departing from the true spirit and scope of the invention as claimed and are, hence, deemed and to be deemed within the full scope of the appended claims.

We claim:

1. A method of treating hair loss disorders and increasing hair arowth in a mammalian subject, the method comprising administering to those areas of skin of the subject manifesting undesirable hair thinning or loss or for which additional hair thickening or growth is desired a therapeutically effective amount of a hair promotion composition comprising one or more aryl alkanones, in a dermatologically or topically acceptable carrier, said one or more aryl alkanones having the following structure:

wherein $R_1$, $R_2$, $R_3$, $R_4$ and $R_5$ which may be the same or different, are independently H, OH, alkyl or alkoxy wherein the alkyl or alkoxy groups are linear or branched and have from 1 to 8 carbon atoms and $R_6$ is H, $COCH_3$ or $CO_2R_7$, and wherein $R_7$ is a linear or branched alkyl having 1 to 8 carbon atoms.

2. The method of claim 1, wherein the one or more aryl alkanones have IL-17 inhibitory activity.

3. The method of claim 1, wherein the one or more aryl alkanones regulates one or more growth factors linked to hair growth.

4. The method of claim 3, wherein the growth factors are Platelet Derived Growth Factors (PDGF), Insulin Growth Factors (IGsI), Vascular Endothelial Growth Factors (VEGFs), or Fibroblast growth factors (FGFs).

5. The method of claim 1, wherein the hair loss disorder is selected from androgenetic alopecia (AGA), non-scarring alopecia, scarring alopecia, male and female pattern AGA, alopecia areata (AA), alopecia totalis (AT), alopecia universalis (AU), eyebrow alopecia, eyelash alopecia, male pattern hair loss, female pattern hair loss, hypotrichosis, hereditary hypotrichosis simplex, frontal fibrosing alopecia, cicatricial alopecia, folliculitis decalvans, tufted folliculitis, dissecting cellulitis of the scalp, ring alopecia, chemotherapy induced alopecia, superficial or deep infections of the scalp, or tinea capitis.

6. The method of claim 1, wherein the subject is a human.

7. The method of claim 1, wherein the hair promotion composition is applied to an alopecic area of the body.

8. The method of claim 1, wherein the hair promotion composition is applied to the scalp, an eyebrow area, or an eyelash area of the subject.

9. The method of claim 2, wherein the IL-17 inhibitory activity is IL-17A inhibitory activity.

10. The method of claim 1, wherein $R_1$, $R_2$, $R^3$, $R_4$ and $R_5$, which may be the same or different, are independently H, OH, alkyl or alkoxy wherein the alkyl or alkoxy groups are linear or branched and have from 1 to 4 carbon atoms.

11. The method of claim 1, wherein $R_1$, $R_2$, and $R_5$ are H and $R_4$ is an alkyl or alkoxy group having 1 to 8 carbon atoms, and $R_6$ is $COCH_3$ or $CO_2C_2H_5$.

12. The method of claim 11, wherein $R_4$ is $OCH_3$.

13. The method of claim 1, wherein $R_1$ and $R_5$ are H.

14. The method of claim 13, wherein the one or more aryl alkanones is selected from the group consisting of:

Compound 1: $R_2$ is H; $R_3$ is OH; $R_4$ is $OCH_3$; and $R_6$ is $COCH_3$;

Compound 2: $R_2$ is H; $R_3$ is OH; $R_4$ is $OCH_3$; and $R_6$ is $CO_2C_2H_5$;

Compound 3: $R_2$ and $R_4$ are H; $R_3$ is OH; and $R_6$ is $COCH_3$;

Compound 4: $R_2$ and $R_4$ are H; $R_3$ is OH; and $R_6$ is $CO_2C_2H_5$;

Compound 5: $R_2$ and $R_4$ are $OCH_3$; $R_3$ is OH; and $R_6$ is $COCH_3$;

Compound 6: $R_2$ and $R_4$ are $OCH_3$; $R_3$ is OH; and $R_6$ is $CO_2C_2H_5$;

Compound 7: $R_2$, $R_3$ and $R_4$ are $OCH_3$; and $R_6$ is $COCH_3$;

Compound 8: $R_2$, $R_3$ and $R_4$ are $OCH_3$; and $R_6$ is $CO_2C_2H_5$;

Compound 9: $R_2$ and $R_4$ are H; $R_3$ is $OCH_3$; and $R_6$ is $CO_2C_2H_5$;

Compound 10: $R_2$ and $R_4$ are H; $R_3$ is $OCH_3$; and $R_6$ is $COCH_3$;

Compound 11: $R_2$ is H; $R_3$ and $R_4$ are $OCH_3$; and $R_6$ is $COCH_3$;

Compound 12: $R_2$ and $R_4$ are H; $R_3$ is OH; and $R_6$ is H; and

Compound 13: $R_2$ and $R_4$ are H; $R_3$ is $OCH_3$; and $R_6$ is H.

15. The method of claim 1, wherein the one or more aryl alkanones is or includes acetyl zingerone.

16. The method of claim 1, wherein the hair promotion composition further comprises one or more non-aryl alkanone hair growth promoter or stimulator.

17. The method of claim 1, wherein the hair promotion composition further comprises a linoleic component selected from one or more of linoleic acids, linoleic esters, linoleic glycosides, linoleic glycerides and/or linoleic triglycerides.

18. The method of claim 1, wherein the dermatologically acceptable carrier is a cosmetic or hair care product and the one more aryl alkanones is present in an amount of from 0.01 to 20 weight percent based on the total weight of the composition.

19. The method of claim 18, wherein the cosmetic or hair care product is selected from shampoos, conditioners, eyebrow fillers, moisturizing compositions, and sunscreens.

20. A method of treating hair loss disorders and increasing hair growth in a mammalian subject, the method comprising administering to those areas of skin of the subject manifesting undesirable hair thinning or loss or for which additional haft thickening or growth is desired a therapeutically effective amount of acetyl zingerone.

\* \* \* \* \*

UNITED STATES PATENT AND TRADEMARK OFFICE
CERTIFICATE OF CORRECTION

| | | |
|---|---|---|
| PATENT NO. | : 11,865,087 B2 | Page 1 of 1 |
| APPLICATION NO. | : 17/392223 | |
| DATED | : January 9, 2024 | |
| INVENTOR(S) | : Ratan K. Chaudhuri | |

It is certified that error appears in the above-identified patent and that said Letters Patent is hereby corrected as shown below:

In the Claims

At Column 23, Line 23 the word "arowth" should be --growth--.

Signed and Sealed this
Fifteenth Day of October, 2024

Katherine Kelly Vidal
*Director of the United States Patent and Trademark Office*